United States Patent
Mestha et al.

(10) Patent No.: US 9,986,923 B2
(45) Date of Patent: *Jun. 5, 2018

(54) SELECTING A REGION OF INTEREST FOR EXTRACTING PHYSIOLOGICAL PARAMETERS FROM A VIDEO OF A SUBJECT

(71) Applicant: Xerox Corporation, Norwalk, CT (US)

(72) Inventors: Lalit Keshav Mestha, Fairport, NY (US); Martin Edward Hoover, Rochester, NY (US); Survi Kyal, Rochester, NY (US)

(73) Assignee: Xerox Corporation, Norwalk, CT (US)

( * ) Notice: Subject to any disclaimer, the term of this patent is extended or adjusted under 35 U.S.C. 154(b) by 473 days.

This patent is subject to a terminal disclaimer.

(21) Appl. No.: 14/593,271

(22) Filed: Jan. 9, 2015

(65) Prior Publication Data

US 2016/0198965 A1   Jul. 14, 2016

(51) Int. Cl.
*A61B 5/024* (2006.01)
*A61B 5/00* (2006.01)

(52) U.S. Cl.
CPC ........ *A61B 5/02433* (2013.01); *A61B 5/0013* (2013.01); *A61B 5/725* (2013.01);
(Continued)

(58) Field of Classification Search
None
See application file for complete search history.

(56) References Cited

U.S. PATENT DOCUMENTS 7,628,760 B2 * 12/2009 Semler ............... A61B 5/02007
600/309
2009/0105556 A1 * 4/2009 Fricke ................. A61B 5/0059
600/301

(Continued)

OTHER PUBLICATIONS

Telgarsky. "Cominant Frequency Extraction" Jun. 1, 2013, Department of Mathematics, Central New Mexico Community College. Obtained from Cornell University Library Online.*

(Continued)

*Primary Examiner* — Katherine Fernandez
*Assistant Examiner* — Yi-Shan Yang
(74) *Attorney, Agent, or Firm* — Philip E. Blair; Fleit Gibbons Gutman Bongini & Bianco P.L.

(57) ABSTRACT

What is disclosed is a system and method for selecting a region of interest for extracting physiological parameters from a video of a subject. In one embodiment the present method involves performing the following. First, time-series signals are received which have been generated by having processing image frames of a video of a subject captured using a single band video camera with a bandpass filter with a pass band in a wavelength range of 495-565 nm and/or 800-1000 nm. The regions of interest are areas where a plethysmographic signal can be detected by the camera. Each time-series signal is associated with a different region of interest. A signal strength is then calculated for each of the time-series signals. The region associated with the time-series signal having a highest signal strength is selected. The time-series signal associated with the selected region can be processed to extract a videoplethysmographic (VPG) signal containing physiological parameters.

5 Claims, 5 Drawing Sheets

(52) U.S. Cl.
CPC .......... *A61B 5/7203* (2013.01); *A61B 5/7225* (2013.01); *A61B 5/748* (2013.01); *A61B 2576/00* (2013.01)

(56) References Cited

U.S. PATENT DOCUMENTS

| | | | | |
|---|---|---|---|---|
| 2010/0204550 | A1* | 8/2010 | Heneghan | A61B 5/0205 |
| | | | | 600/301 |
| 2011/0190598 | A1* | 8/2011 | Shusterman | G06Q 50/22 |
| | | | | 600/301 |
| 2011/0251493 | A1* | 10/2011 | Poh | G06K 9/00255 |
| | | | | 600/477 |
| 2013/0345568 | A1* | 12/2013 | Mestha | A61B 5/7235 |
| | | | | 600/473 |
| 2014/0316292 | A1* | 10/2014 | McRae | A61B 5/0295 |
| | | | | 600/504 |

OTHER PUBLICATIONS

Mestha et al., "System and Method for Determining Arterial Pulse Wave Transit Time", U.S. Appl. No. 14/204,397, filed Mar. 11, 2014.

Mestha et al., "Determining Arterial Pulse Transit Time From Time-Series Signals Obtained at Proximal and Distal Arterial Sites", U.S. Appl. No. 14/515,618, filed Oct. 16, 2014.

Kyal et al., "Discriminating Between Atrial Fibrillation and Sinus Rhythm in Physiological Signals Obtained From Video", U.S. Appl. No. 14/242,322, filed Apr. 1, 2014.

* cited by examiner

US 9,986,923 B2

SELECTING A REGION OF INTEREST FOR EXTRACTING PHYSIOLOGICAL PARAMETERS FROM A VIDEO OF A SUBJECT

TECHNICAL FIELD

The present invention is directed to systems and methods for selecting a region of interest for extracting physiological parameters from a video of a subject.

BACKGROUND

Monitoring cardiac events is of clinical importance in the early detection of potentially fatal conditions. Current technologies involve contact sensors that the individual must wear. Such a requirement can lead to patient discomfort, dependency, loss of dignity, and further may fail due to a variety of reasons including refusal to wear the monitoring device. Elderly cardiac patients are more likely to suffer from the adverse effects of such cardiac monitoring methods. The ability to monitor cardiac function by non-contact means is highly desirable in the healthcare industry.

Accordingly, what is needed in this art are sophisticated systems and methods for automatically selecting best region of interest for extracting physiological parameters from a video of a subject.

INCORPORATED REFERENCES

The following U.S. patents, U.S. patent applications, and Publications are incorporated herein in their entirety by reference.

"System And Method For Determining Arterial Pulse Wave Transit Time", U.S. patent application Ser. No. 14/204,397, by Mestha et al.

"Determining Arterial Pulse Transit Time From Time-Series Signals Obtained At Proximal And Distal Arterial Sites", U.S. patent application Ser. No. 14/515,618, by Mestha et al.

"Discriminating Between Atrial Fibrillation And Sinus Rhythm In Physiological Signals Obtained From Video", U.S. patent application Ser. No. 14/242,322, by Kyal et al.

BRIEF SUMMARY

What is disclosed is a system and method for selecting a region of interest for extracting physiological parameters from a video of a subject. In one embodiment the present method involves performing the following. First, a plurality of time-series signals are received which have been generated by processing image frames of a video of a subject captured using a single band video camera with a bandpass filter with a pass band in a wavelength range of 495-565 nm and/or 800-1000 nm. The regions of interest are those areas where a plethysmographic signal can be detected by the video camera. Each time-series signal is associated with a different region of interest. A signal strength is then calculated for each of the time-series signals. The region that is associated with the time-series signal having a highest signal strength is selected. The time-series signal associated with the selected region can be processed to extract a VPG (videoplethysmographic) signal containing physiological parameters. Features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

What is disclosed is a system and method for selecting a region of interest for extracting physiological parameters from a video of a subject.

Non-Limiting Definitions

"Plethysmography" is the study of relative blood volume changes in blood vessels which reside beneath the surface of skin tissue.

A "photoplethysmographic (PPG) signal" is a plethysmographic signal obtained using an optical instrument which captures the blood volume pulse over time.

A "videoplethysmographic (VPG) signal" is a plethysmographic signal extracted from processing batches of image frames of a video of the skin surface.

Figure 1:
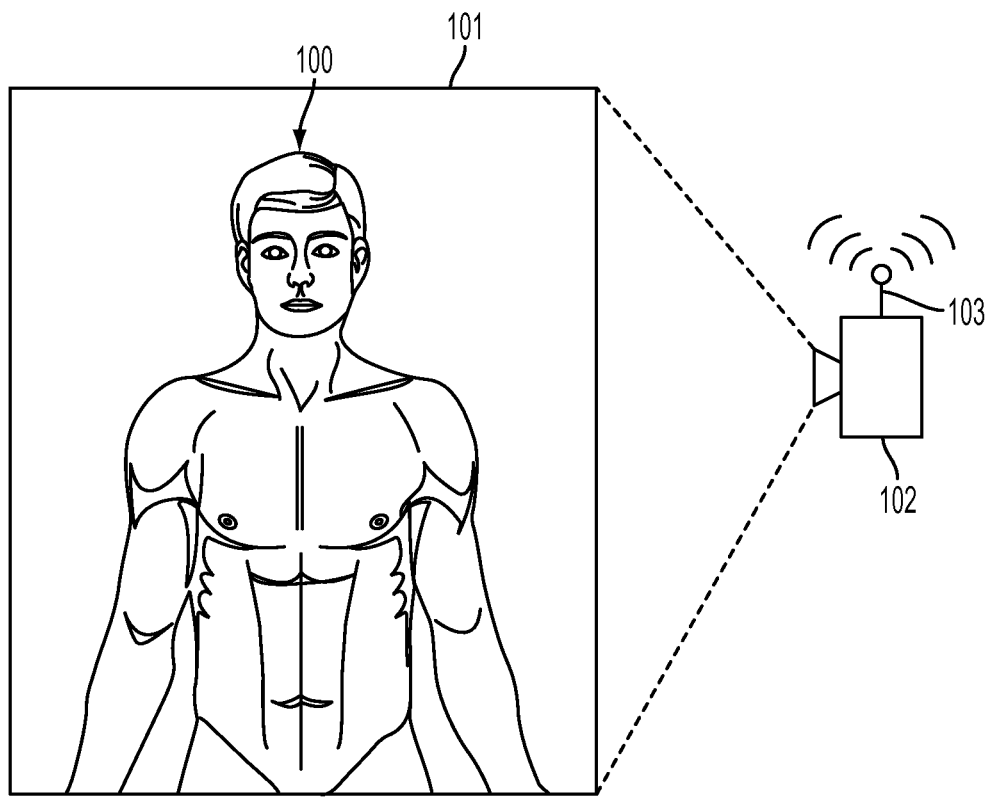
FIG. 1 shows a video image device actively acquiring video image frames of a subject.

A "subject" refers to a living being. One example subject 100 is shown in FIG. 1. Although the term "person" or "patient" may be used throughout this disclosure, it should be appreciated that the subject may be something other than a human such as, for example, a primate. Therefore, the use of such terms is not to be viewed as limiting the scope of the appended claims strictly to humans.

A "video", as is generally understood, refers to a plurality of time-sequential image frames captured by a video imaging device of an area of exposed skin of a subject where a plethysmographic signal corresponding to the subject's cardiac function can be registered by the video camera used to capture that video.

A "video imaging device", as used herein, is a single band video camera with a bandpass filter with a pass band in a wavelength range of 495-565 nm and/or 800-1000 nm. FIG. 1 shows an example video imaging device 102 with a filter (not shown) acquiring video 101 of a subject 100. Image frames of the video may be communicated to a remote device via a wireless communication element 103, shown as an antenna. The video camera may comprise one or more lens which function to focus received reflected light. Focused and filtered light is directed on to one or more photodetectors which independently record intensity values at multiple pixel locations along a multi-dimensional grid. The received light is spatially resolved to form an image. Video cameras typically have a plurality of outputs for retrieving image frames of the video and may further incorporate components such as memory, one or more storage devices, and one or more processors executing machine readable program instructions for analyzing batches of image frames in real-time in accordance with the teachings hereof. The image frames can also be retrieved from a remote device over a network, retrieved from a media such as a CDROM or DVD, or downloaded from a web-based system or application which makes video image frames available for processing. Image frames can also be received from an application such as those which are available for handheld cellular devices and processed on the smartphone or other handheld computing device such as an iPad or Tablet-PC. Video devices comprising a single band video camera with a bandpass filter are readily available in various streams of commerce.

Figure 2:
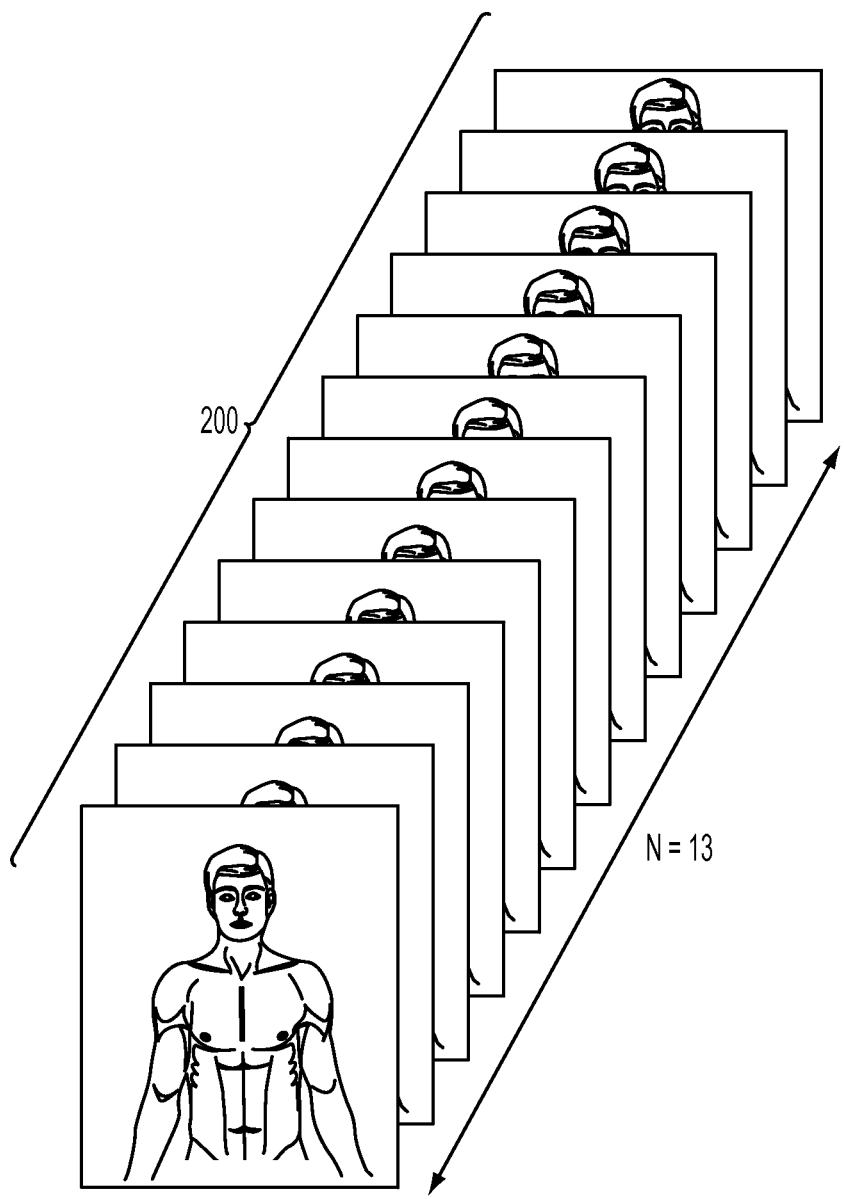
FIG. 2 shows a batch of image frames of the video acquired by the video imaging device of FIG. 1.

A "batch of image frames" refers to a plurality of time-sequential image frames which are processed to isolate various regions of exposed skin for selection in a manner as disclosed herein. FIG. 2 shows an example batch of N=13 image frames (collectively at 200) acquired by the video imaging device 102 of FIG. 1. Batches of image frames do not have to be the same size and may vary dynamically during processing. A size of a given batch of image frames should at least be of a duration which captures one cardiac cycle of the subject. Batches of image frames can be processed utilizing a sliding window. In one example, the sliding window defines 1 second of new image frames overlapping 29 seconds of image frames from the previous batch, (i.e., a 96% overlap). The size of the sliding window may be dynamically adjusted in real-time as needed. Image frames of a given batch are analyzed to identify and isolate regions of interest.

Figure 3:
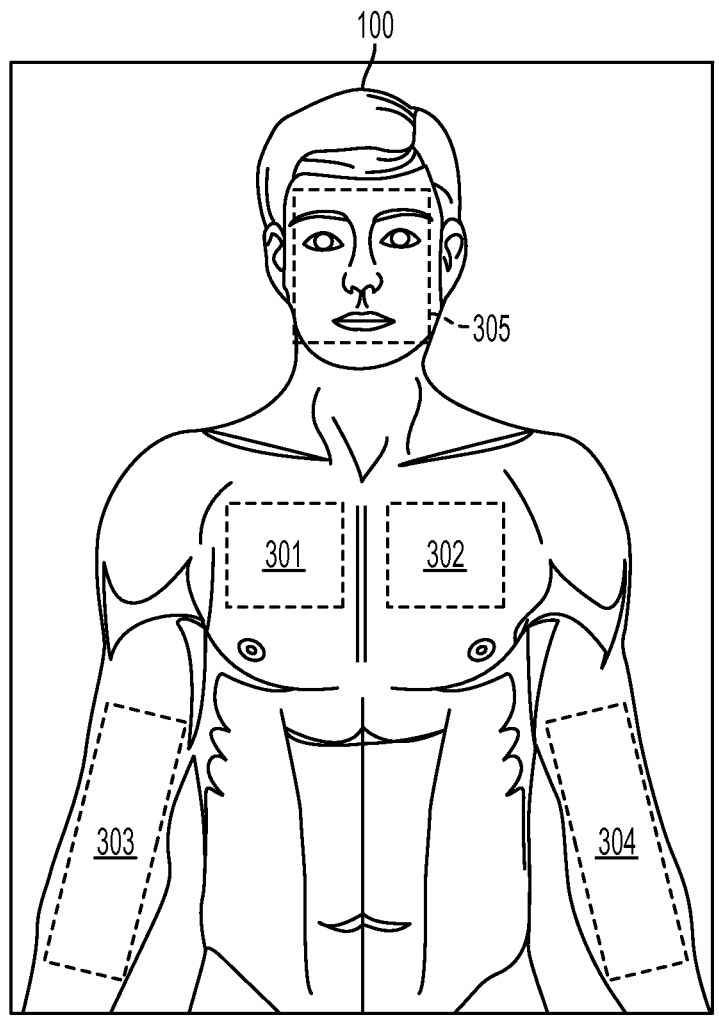
FIG. 3 shows one of the image frames of the batch of FIG. 2 wherein various regions of exposed skin have been isolated.

"A region of interest" refers to at least a partially unobstructed view of the subject's exposed skin tissue as seen through the lens of the video imaging device used to acquire video of the subject. FIG. 3 shows one of the image frames of the batch of image frame of FIG. 2 wherein various regions of interest (denoted 301, 302, 303, 304 and 305) have been isolated. It should be appreciated that the regions of interest of FIG. 3 are for explanatory purposes and that other regions of interest may be identified or otherwise selected. Also regions of interest can be irregular shape. As such, FIG. 3 should not be viewed as limiting the scope of the appended claims solely to the illustrated regions. A region of interest can be identified in a given image frame using image processing techniques which include, for example, color and texture identification, object identification, thoracic region recognition, spatial feature analysis, spectral information, pattern recognition, face detection methods, and facial recognition algorithms. Moreover, a user or technician may use a mouse or, for instance, a touchscreen display to identify regions of interest in the image frames. Regions of interest do not have to be the same size. The size of a given region of interest will vary depending on the application. Pixels in a given region of interest are isolated in the image frames of the video using techniques which include, for instance, pixel classification, object identification, thoracic region recognition, color, texture, spatial features, spectral information, pattern recognition, face detection, facial recognition, and a user input. Pixels may be weighted, averaged, normalized, or discarded, as needed. Pixels in each of the isolated regions of interest in a batch of image frames are processed to obtain a time-series signal associated with each region.

A "time-series signal" is a signal that contains frequency components that relate to the subject's cardiac function. The time-series signal contains the sum total of the relative blood volume changes in the blood vessels close to the skin surface within the isolated region. These arterial pulsations comprise a dominant component of the time-series signals. In one embodiment, a time-series signal is obtained by averaging the values of all pixels in the isolated region of interest to obtain a channel average on a per-frame basis. Then, for each channel, a global channel average is computed by adding the channel averages across multiple image frames and dividing by the total number of frames comprising the batch. The channel average is subtracted from the global channel average and the result is divided by a global channel standard deviation to obtain the time-series signal for that particular region. Time-series signals may be detrended to remove non-stationary components. Automatic peak detection may also be employed. A VPG signal can be extracted from the time-series signal by performing signal separation. Methods for extracting a VPG signal from a time-series signal are disclosed in the incorporated references by Mestha and Kyal.

A "window of frequencies" is defined about a dominant frequency $f_0$ and may further include harmonic frequencies given by: $2f_0, 3f_0, 4f_0, \ldots,$ . A dominant frequency $f_0$ can be identified in a signal by computing a power spectral density using, for example, a non-parametric spectral density estimation or a parametric spectral density estimation technique which are well understood in the signal processing arts. The power spectral density describes how the power is distributed over different frequencies in a signal. In general, the power P of signal x(t) can be determined over time interval [−T, T] as follows:

$$P = \lim_{T \to \infty} \frac{1}{2T} \int_{-T}^{T} x(t)^2 dt$$

"Signal strength", for the purposes hereof, is calculated over frequencies within a band of interest. Frequencies within the window of frequencies collectively define the band of interest. Signal strength can be determined by pulse harmonic strength (PHS). In one embodiment PHS is given by:

$$PHS = \frac{P_{sig}}{P_{noise}},$$
$$P_{noise} = P_{Total} - P_{sig}.$$

where $P_{sig}$ is the power in the band of interest, and $P_{noise}$ is the power in all remaining bands. This metric is preferable because the power of the blood volume pulse is centered on the beat of the subject's heart and the various harmonics of those beats.

Signal strength can also be determined by signal-to-noise ratio (SNR). In one embodiment, SNR is given by:

$$SNR = \frac{P_{sig}}{P_{total}},$$

where $P_{sig}$ is the power in the band of interest, and $P_{total}$ is the total power in the time-series signal.

"Receiving signals" is intended to be widely construed and includes: retrieving, capturing, acquiring, or otherwise obtaining signals for processing in accordance with the methods disclosed herein. Signals can be retrieved from a memory or storage device, retrieved from a media such as a CDROM or DVD, obtained from a remote device over a network, or downloaded from a web-based system or application which makes such signals available.

It should be appreciated that the steps of "determining", "analyzing", "identifying", "receiving", "processing", "calculating", "selecting", "performing" and the like, as used herein, include the application of various signal processing and mathematical operations applied to data and signals, according to any specific context or for any specific purpose. It should be appreciated that such steps may be facilitated or otherwise effectuated by a microprocessor executing machine readable program instructions retrieved from a memory or storage device.

EXAMPLE FLOW DIAGRAM

Figure 4:
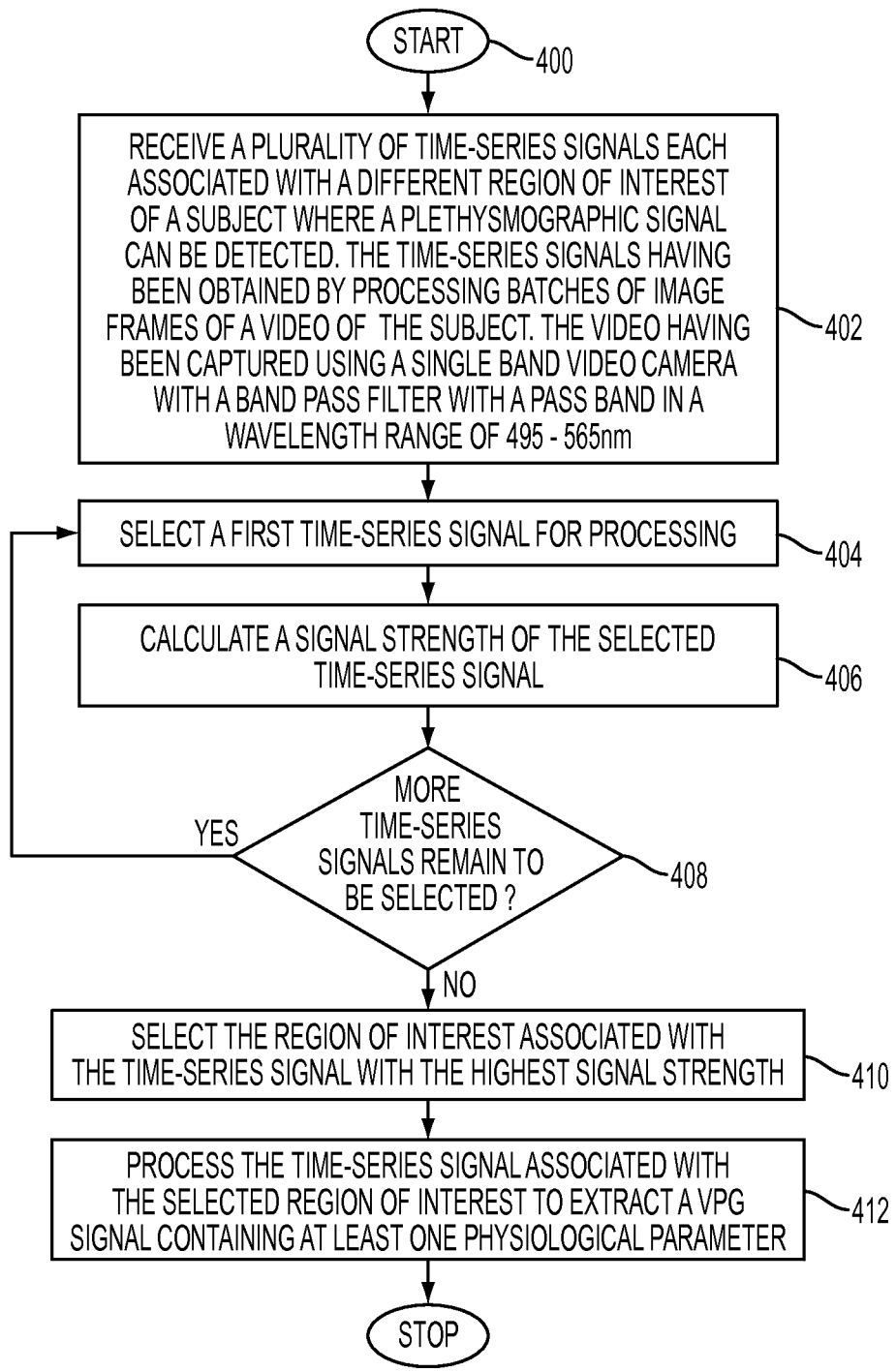
FIG. 4 is a flow diagram which illustrates one embodiment of the present method for selecting a region of interest for extracting physiological parameters from a video of the subject of FIG. 1.

Reference is now being made to the flow diagram of FIG. 4 which illustrates one example embodiment of the present method for selecting a region of interest for extracting physiological parameters from an area of exposed skin. Flow processing begins at step 400 and immediately proceeds to step 402.

At step 402, receive a plurality of time-series signals each associated with a different region of interest of a subject where a plethysmographic signal can be detected. The time-series signals having been obtained by processing batches of image frames of a video of the subject. The video having been captured using a single band video camera with a bandpass filter with a pass band in a wavelength range of 495-565 nm and/or 800-1000 nm. Various different regions of interest are shown and discussed with respect to FIG. 3.

At step 404, select a first time-series signals for processing. The selection can be automatically made by a microprocessor executing machine readable program instructions to make such a selection or, alternatively, by a user using the display and keyboard of a workstation.

At step 406, calculate a signal strength of the selected time-series signal. Methods for computing the strength of a given signal are disclosed herein.

At step 408, a determination is made whether more time-series signals remain to be selected for processing. If so, then processing continues with respect to step 404 wherein a next of time-series signal of the received plurality of signals is selected. A signal strength of the next selected time-series signal is then computed. Processing repeats in a similar manner until no more time-series signals remain to be selected.

At step 410, select the region of interest associated with the time-series signal with the highest signal strength.

At step 412, process the time-series signal associated with the selected region of interest (selected in step 410) to extract a VPG signal containing at least one physiological parameter of the subject. Thereafter, in this embodiment, further processing stops.

It should also be appreciated that the flow diagrams depicted herein are illustrative. One or more of the operations may be performed in a differing order. Other operations may be added, modified, enhanced, or consolidated. Variations thereof are intended to fall within the scope of the appended claims.

EXAMPLE NETWORKED SYSTEM

Figure 5:
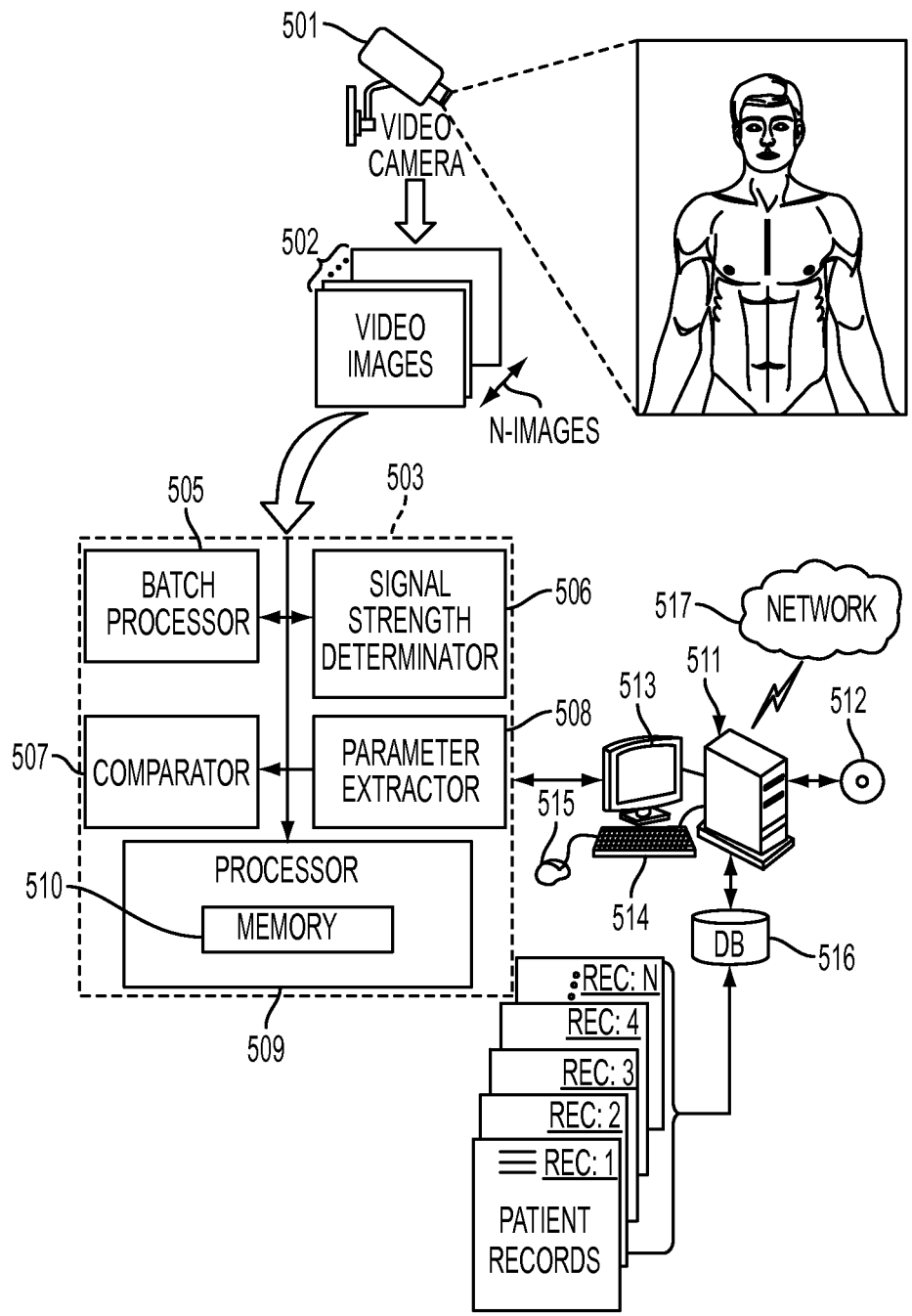
FIG. 5 which illustrates a block diagram of one example system for performing various aspects of the teachings hereof as described with respect to the flow diagram of FIG. 4.

Reference is now being made to FIG. 5 which illustrates a block diagram of one example system for performing various aspects of the teachings hereof.

In FIG. 5, the single band video camera 501 with a bandpass filter with a pass band in a wavelength range of 495-565 nm and/or 800-1000 nm is shown acquiring video of the subject of FIG. 1. The image frames comprising the video (collective at 502) are communicated to the image processing system 503. Batch Processor 505 receives the batch of image frames and isolates pixels associated with the exposed body region in the image frames to obtain a time-series signal for each region of interest. In other embodiments, the Batch Processor is further enabled to extract a VPG signal from each of the time-series signals. Signal Strength Determinator 506 receives each of the time-series signals from the Batch Processor and proceeds to calculate a signal strength for each using the methods disclosed herein. Comparator 507 then compares each of the signal strengths determined for each of the time-series signals to identify which had the highest strength. Parameter Extractor 508 proceeds to process the VPG signal associated with the identified region of interest to extract one or more physiological parameters for the subject. Processor 509 executes machine readable program instructions operating alone or in conjunction with other processors and Memory 510, to assist or otherwise perform the functionality of any of the modules of system 503. Processor 509 further facilitates communication with the workstation 511.

A computer case of the workstation houses various components such as a motherboard with a processor and memory, a network card, a video card, a hard drive capable of reading/writing to machine readable media 512 such as a floppy disk, optical disk, CD-ROM, DVD, magnetic tape, and the like, and other software and hardware needed to perform the functionality of a computer system. The workstation further includes a display device 513, such as a CRT, LCD, or touchscreen device, for displaying information, video, measurement data, computed values, medical information, results, locations, and the like. A user can view any of that information and make a selection from menu options displayed thereon. The keyboard and mouse effectuate a user input or selection. The workstation implements a database in storage device 516 wherein patient records are stored, manipulated, and retrieved in response to a query. Such records, in various embodiments, take the form of patient medical histories. Although the database is shown as an external device, the database may be internal to the workstation mounted, for example, on a hard disk within the computer case.

It should be appreciated that the workstation has an operating system and other specialized software configured to display alphanumeric values, menus, scroll bars, dials, slideable bars, pull-down options, selectable buttons, and the like, for entering, selecting, modifying, and accepting information needed for processing image frames to obtain time-series signals and VPG signals in accordance with the methods disclosed herein. The workstation is further enabled to display image frames. A user or technician may use the workstation to identify regions of interest, set parameters, select image frames and/or regions of interest for processing. Such user entries may be stored/retrieved in a storage devices 512 and 516 along with default settings, initial parameter values, and the like. A user may adjust the various parameters employed or dynamic settings in real-time as successive batches of image frames are processed. Although shown as a desktop computer, it should be appreciated that the workstation can be a laptop, mainframe, or a special purpose computer such as an ASIC, circuit, or the like. The embodiment of the workstation of FIG. 5 is illustrative and may include other functionality known in the arts.

Any of the components of the workstation may be placed in communication with the video processing system 503 or any devices in communication therewith. Moreover, any of the modules and processing units of system 503 can be placed in communication with storage devices 512 and/or 516 and may store/retrieve therefrom data, variables, records, parameters, functions, and/or machine readable/ executable program instructions, as needed to perform their intended functionality.

Each of the modules of the system of FIG. 5 may be placed in communication with one or more remote devices over a network 517. It should be appreciated that some or all of the functionality performed by any of the modules or processing units of system 503 can be performed, in whole or in part, by the workstation placed in communication with the video imaging device 501 over network 517. The embodiment shown is illustrative and should not be viewed as limiting the scope of the appended claims strictly to that configuration. Various modules may designate one or more components which may, in turn, comprise software and/or hardware designed to perform the intended function.

The teachings hereof can be implemented in hardware or software using any known or later developed systems, structures, devices, and/or software by those skilled in the applicable art without undue experimentation from the functional description provided herein with a general knowledge of the relevant arts. One or more aspects of the methods described herein are intended to be incorporated in an article of manufacture which may be shipped, sold, leased, or otherwise provided separately either alone or as part of a product suite or a service.

It will be appreciated that the above-disclosed and other features and functions, or alternatives thereof, may be desirably combined into other different systems or applications. Presently unforeseen or unanticipated alternatives, modifications, variations, or improvements may become apparent and/or subsequently made by those skilled in this art which are also intended to be encompassed by the following claims. The teachings of any textbooks, papers, or other publications referenced herein are each hereby incorporated herein in their entirety by reference.

What is claimed is:

1. A system for selecting a region of exposed skin to extract at least one physiological parameter from a video of a subject, the system comprising:
   a single band video camera with a bandpass filter for acquiring video of the subject, the video comprising a plurality of time-sequential image frames of an area of exposed skin of the subject, each of the time-sequential image frames comprising a plurality of pixels, the bandpass filter having a pass band in a wavelength range of 495-565 nm and/or 800-1000 nm; and
   a processor executing machine readable instructions which configure the processor to:
      analyze the time-sequential image frames to identify a plurality of regions of exposed skin of the subject where a plethysmographic signal can be detected;
      for each of the plurality of regions of exposed skin:
         process the pixels to obtain an associated time-series signal corresponding to relative blood volume changes in blood vessels close to a surface of the exposed skin within the region of interest;
      for each of the obtained time-series signals:
         compute a power spectral density of the time-series signal;
         identify a dominant frequency;
         identify harmonic frequencies of the dominant frequency;
         define a window of frequencies about the dominant frequency, frequencies within the window collectively defining a band of interest; and
         calculate a signal strength for the time-series signal over the band of interest;
      determine which of the time-series signals has a highest signal strength;
      select, automatically, one of the plurality of regions of exposed skin of the subject associated with the time-series signals having the highest signal strength; and
      extract at least one physiological parameter from the selected one of the plurality of regions of exposed skin.

2. The system of claim 1, wherein the power spectral density is computed by at least one of: a non-parametric spectral density estimation on a filtered time-series signal, and a parametric spectral density estimation on a filtered time-series signal.

3. The system of claim 1, wherein the pulse harmonic strength (PHS) at least comprises:

$$PHS = \frac{P_{sig}}{P_{noise}},$$

where $P_{sig}$ is power in said band of interest, and $P_{noise}$ is power in all remaining bands of said time-series signal, and wherein a signal-to-noise ratio (SNR) at least comprises:

$$SNR = \frac{P_{sig}}{P_{total}},$$

where $P_{total}$ is total power in said time-series signal.

4. The system of claim 1, wherein the processor is further configured to detrend at least one of the time-series signals to remove non-stationary components.

5. The system of claim 1, further comprises determining whether a subject is having an atrial fibrillation event by
   defining a size N of a batch of image frames such that $N_{min} \leq N \leq N_{max}$, where $N_{min}$ is a minimum size of a batch of image frames and $N_{max}$ is a maximum size of a batch of image frames; and
   for each batch of image frames of size N:
      processing this batch of image frames to isolate pixels associated with said region of exposed skin;
      processing said isolated pixels to obtain a time-series signal for this batch;
      extracting a VPG signal from said time-series signal;
      computing a power spectral density across all frequencies within said VPG signal;
      calculating a pulse harmonic strength for this VPG signal;
      comparing the pulse harmonic strength (PHS) to a discrimination threshold obtained from a Receiver Operating Characteristic (ROC) curve constructed from health vitals obtained for a group of cardiac patients, said discrimination threshold discriminating between low PHS values and high PHS values; and classifying, as a result of said comparison, that said subject is one of: in atrial fibrillation, and in sinus rhythm, wherein when PHS is below said threshold said subject is classified as being in atrial fibrillation, and in normal sinus rhythm otherwise.

* * * * *